US00PP25825P2

(12) United States Plant Patent
Zary

(10) Patent No.: US PP25,825 P2
(45) Date of Patent: Aug. 25, 2015

(54) ROSE PLANT NAMED 'ZARSUNORGDLT'

(50) Latin Name: *Rosa×hybrida*
Varietal Denomination: ZARsunorgdlt

(71) Applicant: American Daylily and Perennials, Inc., Grain Valley, MO (US)

(72) Inventor: Keith W. Zary, Troy, OH (US)

(73) Assignee: American Daylily and Perennials, Inc., Grain Valley, MO (US)

( * ) Notice: Subject to any disclaimer, the term of this patent is extended or adjusted under 35 U.S.C. 154(b) by 0 days.

(21) Appl. No.: 14/545,448

(22) Filed: May 5, 2015

Related U.S. Application Data

(60) Provisional application No. 61/998,872, filed on Jul. 10, 2014.

(51) Int. Cl.
*A01H 5/00* (2006.01)

(52) U.S. Cl.
USPC ..... Plt./119

(58) Field of Classification Search
USPC ..... Plt./119
See application file for complete search history.

*Primary Examiner* — Annette Para
(74) *Attorney, Agent, or Firm* — Barbara Campbell; Cochran Freund & Young LLC

(57) ABSTRACT

A new rose plant designated 'ZARsunorgdlt' particularly distinguished by being a landscape (miniature) shrub rose having orange flowers with yellow on the lower surface of the flowers, a compact growth habit requiring little pruning, shows resistance to powdery mildew, rust, and black spot, grows vigorously on its own roots, and shown to be heat tolerant and cold hardy in trials, and hardy to USDA Zones 5 to 10, is disclosed.

2 Drawing Sheets

Genus and species: *Rosa×hybrida.*
Variety denomination: 'ZARsunorgdlt'.

BACKGROUND OF THE NEW VARIETY

The present invention comprises a new and distinct variety of rose, botanically known as *Rosa×hybrida*, and hereinafter referred to by the variety name 'ZARsunorgdlt'. 'ZARsunorgdlt' originated from a cross conducted in June 2009 in Somis, Calif. between the female rose variety 'JAChal', also commercially known as 'Sun Sprinkles' (U.S. Plant Pat. No. 11,883), and the male rose variety KNOCK OUT 'RADrazz' (U.S. Plant Pat. No. 11,836).

The seeds from the cross were sown and plants were grown for evaluation. An individual plant designated 'ZARsunorgdlt' was selected in July 2010 in Somis, Calif. 'ZARsunorgdlt' was first vegetatively propagated in July 2010 in Tipp City, Ohio by softwood cuttings rooted under mist. 'ZARsunorgdlt' was found to reproduce true to type in successive generations of asexual propagation via softwood cuttings, hardwood cuttings, and by budding onto rootstock.

SUMMARY

The following are the most outstanding and distinguishing characteristics of this new variety when grown under normal horticultural practices in Somis, Calif., Tipp City, Ohio, Sarasota, Fla., and Grain Valley, Mo.

1. A landscape (miniature) shrub rose having orange flowers with yellow on the lower surface of the flowers;
2. A compact growth habit requiring little pruning;
3. Shows resistance to powdery mildew, rust, and black spot;
4. Strong tendency to produce inflorescence and good color display for an extended period;
5. Grows vigorously on its own roots; and 6. Shown to be heat tolerant and cold hardy in trials, and hardy to USDA Zones 5 to 10.

DESCRIPTION OF THE PHOTOGRAPHS

This new rose plant is illustrated by the accompanying photographs which show the plants' foliage, buds, and flowers. The colors shown are as true as can be reasonably obtained by conventional photographic procedures. The photos of the plants in FIGS. 1 to 2 were taken outdoors in Grain Valley, Mo. in June 2013, and the plants were 2-years-old. The photo of the plant parts in FIG. 3 was taken in Tipp City, Ohio, in September 2014 from a two-year-old plant.

Figure 1:
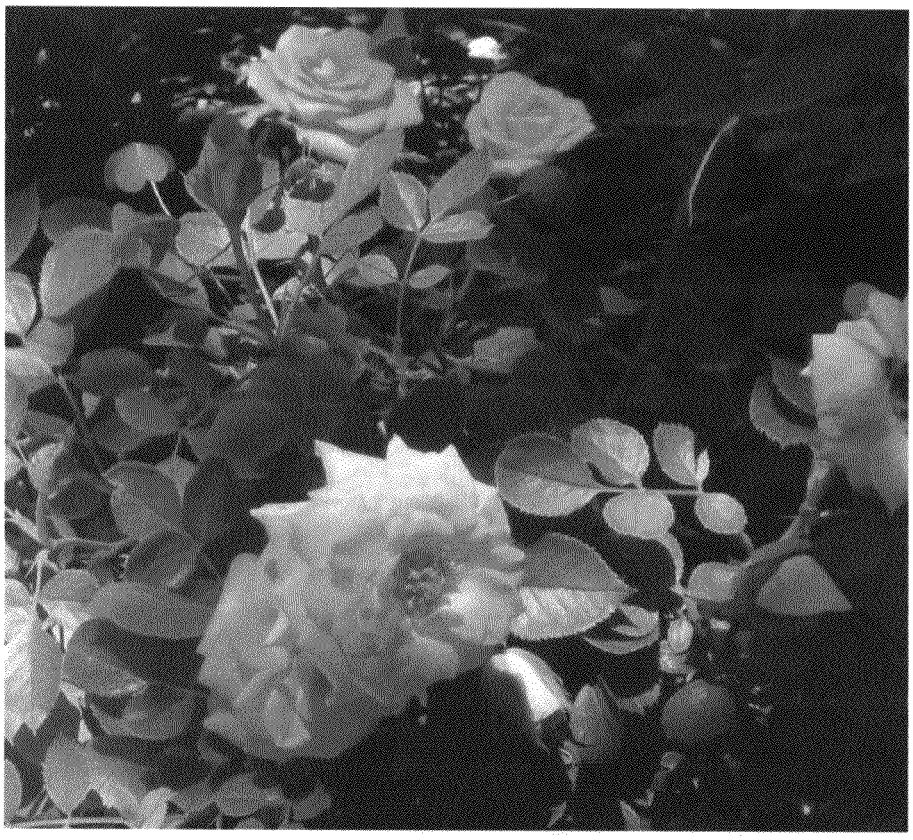
FIG. 1 shows the foliage and flowers opening of 'Zarsunorgdlt'.
Figure 2:
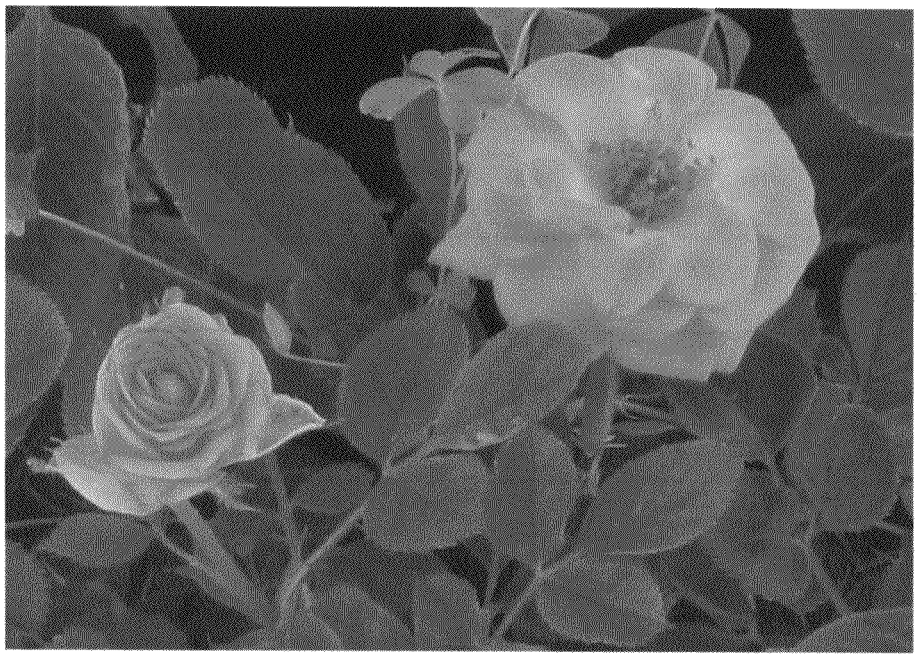
FIG. 2 shows a close-up the flower of 'Zarsunorgdlt'.
Figure 3:
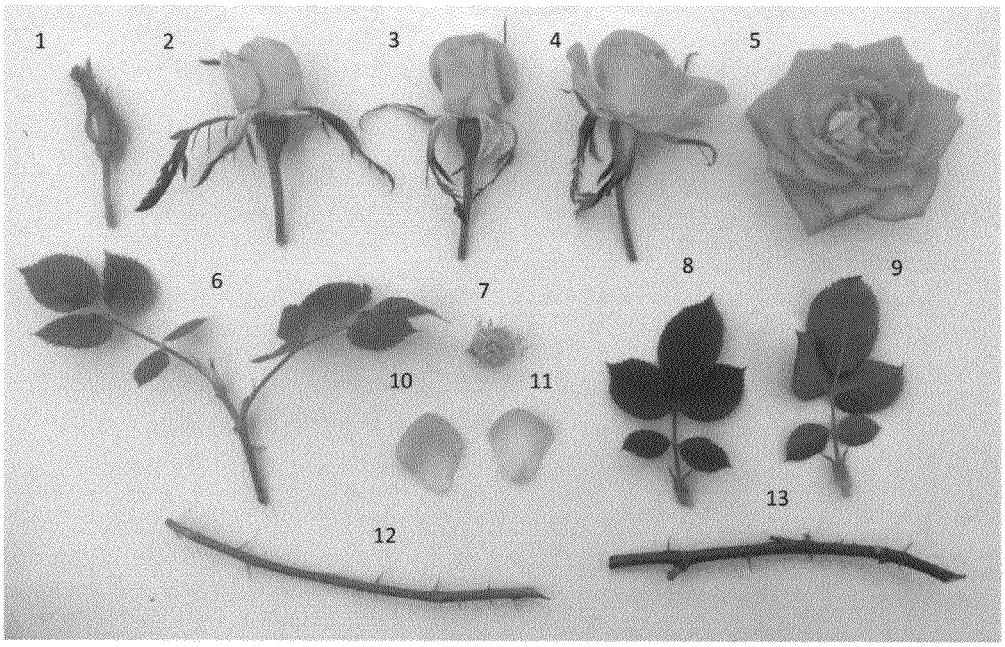
FIG. 3 shows a close-up of individual flower parts of the plant of 'Zarsunorgdlt', where.

1 shows a closed flower bud
2 shows the flower as it is beginning to open
3 shows the flower as it is opening more
4 shows the flower as it is almost open
5 shows a fully opened flower.
6 shows a pair of immature leaves and their leaflets attached to the stem
7 shows the male reproductive parts
8 shows the upper surface of a mature leaf
9 shows the lower surface of a mature leaf
10 shows the upper surface of a petal
11 shows the lower surface of a petal
12 shows a section of an immature stem with thorns
13 shows a section of a mature stem with thorns

DESCRIPTION OF THE NEW VARIETY

The following detailed descriptions set forth the distinctive characteristics of 'ZARsunorgdlt'. The data which define these characteristics were collected from asexual reproductions carried out in Tipp City, Ohio between July to October 2014. Data was collected on 2-year-plants, growing on their own roots, outdoors. The plants were not sprayed and were fertilized at a rate of 100 ppm of Nitrogen, Phosphorous, and Potassium. Color references are to The R.H.S. Colour Chart of The Royal Horticultural Society of London (R.H.S.), (2001).

Classification:

*Family*.—Rosaceae.

*Botanical*.—*Rosa×hybrida*.

*Designation*.—'Zarsunorgdlt'.

Parentage:

*Female parent*.—The female rose variety 'JAChal', also commercially known as 'Sun Sprinkles' (U.S. Plant Pat. No. 11,388).

*Male parent*.—The male rose variety KNOCK OUT 'RADrazz' (U.S. Plant Pat. No. 11,836).

Plant:

*Habit*.—Upright, compact.

*Height*.—30.0 cm.

*Spread*.—24.0 cm.

*Life cycle*.—Perennial.

*Time to produce a rooted cutting*.—3 weeks.

*Root description*.—Fibrous.

*Time to bloom from propagation*.—8 to 10 weeks.

*Lastingness of inflorescence on the plant*.—5 to 6 days.

Lateral branches/peduncles:

*Color*.—RHS 146B (Yellow-Green).

*Pubescence*.—Absent.

*Stem shape*.—Round.

*Diameter*.—0.2 cm.

*Length*.—10.0 cm to 12.0 cm.

*Anthocyanin*.—Absent.

*Thorns*.—Density: 10 per 8 cm of stem. Shape: Straight and needle-shaped. Color: RHS 199B (Greyed-Brown) for mature wood and RHS 193C (Greyed-Green) for young wood. Length: 0.5 cm. Width: 0.1 cm at the base.

Foliage:

*Arrangement*.—Odd pinnate.

*Quantity of leaflets per leaf*.—5.

*Leaf length*.—8.0 cm.

*Leaf width*.—5.0 cm.

*Terminal leaflet*.—Length: 3.0 cm. Width: 2.0 cm. Shape: Elliptic. Apex: Acuminate. Base: Rounded. Margin: Simply serrate. Color, immature leaf: Upper surface: RHS 146B (Yellow-Green). Lower surface: RHS 147C (Yellow-Green) overlain on the immature leaf edges with RHS 178D (Greyed-Red). Color, mature leaf: Upper surface: RHS 137A (Green). Lower surface: RHS N138B (Green). Texture: Upper surface: Glossy, smooth, coriaceous. Lower surface: Smooth.

*Lateral leaflet*.—Length: 2.0 cm. Width: 1.5 cm. Shape: Elliptic. Apex: Acute. Base: Oblique. Margin: Simply serrate. Color, immature leaf: Upper surface: RHS 146B (Yellow-Green). Lower surface: RHS 147C (Yellow-Green) overlain on the immature leaf margins with RHS 178D (Greyed-Red). Color, mature leaf: Upper surface: RHS 137A (Green). Upper surface: RHS N138B (Green). Texture: Upper surface: Glossy, smooth and coriaceous. Lower surface: Smooth.

*Leaf venation pattern*.—Reticulate.

*Leaf venation color*.—Upper surface: RHS 137A (Green). Lower surface: RHS N138B (Green).

*Petioles, leaves*.—Length: 5.0 cm. Diameter: 0.1 cm. Color: RHS 146B (Yellow-Green). Texture: Rough with many prickles and glands. Thorns: 3 on the petiole, slightly curved and 0.1 cm to 0.2 cm in length and RHS 193C (Greyed-Green).

*Petiolule, leaflets*.—Length: 0.1 cm. Diameter: 0.1 cm. Color: RHS N138B (Green). Texture: Smooth. Thorns: None observed.

*Stipules*.—Arrangement and appearance: Parallel, auricles facing slightly downward, adnate. Length: 1.0 cm. Width: 0.3 cm. Shape: Adnate, parallel, auricles facing slightly outward. Apex: Truncate with auricles. Base: Truncate. Margin: Rough with glands. Color, immature leaf: Upper surface: RHS 146D (Yellow-Green) with 0.2 cm at the truncate base of RHS 178D (Greyed-Red). Lower surface: RHS 146D (Yellow-Green) with 0.2 cm at the truncate base of RHS 178D (Greyed-Red). Color, mature leaf: Upper surface: RHS 146B (Yellow-Green). Lower surface: RHS 146B (Yellow-Green). Texture (both upper and lower surfaces): Smooth but edged in glands.

Flowers and inflorescence:

*Appearance and arrangement*.—Borne singly and in small clusters of 3 to 5 flowers.

*Fragrance*.—None observed.

*Diameter of flower*.—4.5 cm when fully open.

*Depth or height*.—1.5 cm when fully open.

*Lastingness of flowers on the plant*.—5 to 6 days.

*Buds*.—Length: 2.0 cm when buds are beginning to open. Width: 1.0 cm when buds are beginning to open. Surface texture: Smooth. Shape: Pointed ovoid. Margin: Entire. Color: RHS 29C (Orange) changing to RHS 29B (Orange) toward the base of the bud.

*Petals*.—Quantity per flower: 30 to 35. Length: 2.0 cm. Width: 2.0 cm. Shape: Orbicular. Apex: Rounded. Base: Rounded. Margin: Entire. Color, when opening: Upper surface: RHS 29C (Orange) on the petal edges and RHS 18A (Yellow-Orange) over the rest of the petal. Lower surface: RHS 20C (Yellow-Orange). Color, when fully opened: Upper surface: RHS 29C (Orange) with RHS 13C (Yellow) at the petal base. Lower surface: RHS 18B (Yellow-Orange). Surface texture (both upper and lower surfaces): Smooth.

*Sepals*.—Quantity per flower: 5, 2 are entire, one is pinnatified on one side 2 are pinnatified on both sides. Length: 1.5 cm. Width: 0.5 cm. Shape: Lanceolate. Apex: Acute to aristate. Base: Truncate. Margin: Either hoary or hoary and pinnatified. Color, when opening: Upper surface: RHS 191C (Greyed-Green). Lower surface: RHS 146B (Green) with an overlay of RHS 183D (Greyed-Purple) in areas exposed to direct sun. Color, when fully open: Upper surface: RHS 191C (Greyed-Green). Lower surface: RHS 146B (Green). Surface texture: Upper surface: Glandular. Lower surface: Hoary.

Reproductive organs:

*Stamens*.—Quantity per flower: 35 to 40. Anther color: RHS 16C (Yellow-Orange). Filament length: 0.4 cm. Pollen amount: Sparse. Pollen color: RHS 163A (Greyed-Orange).

*Pistils*.—Quantity per flower: 30. Pistil length: 0.3 cm. Stigma shape: Orbicular. Stigma color: RHS 156D (Greyed-White). Style length: 0.2 cm. Style color:

RHS 180D (Greyed-Red). Receptacle: Height: 0.5 cm. Diameter: 0.7 cm. Color: RHS 146B (Yellow-Green). Texture: Smooth.

Fruit and seed set: None observed.

Disease and pest/insect resistance: Resistant to the common rose diseases of powdery mildew, rust, and black spot.

COMPARISON WITH PARENTAL LINES AND COMMERCIAL VARIETY

'Zarsunorgdlt' is a distinct variety of rose and is distinguished from its parents as described in Table 1.

TABLE 1

Comparison with Parental Lines

| Characteristic | 'Zarsunorgdlt' | Female Parent 'JAChal' | Male Parent KNOCK OUT 'RADrazz' |
|---|---|---|---|
| Plant height and width | 30 cm in height and 24 cm in width | 50 cm to 60 m in height and 45 cm to 50 cm in width | 150 cm in height and 120 cm in width |
| Flower color | RHS 29C (Yellow-Orange) | RHS 12A (Yellow) | RHS 53C (Red) to RHS 53D (Red) |

'Zarsunorgdlt' is a distinct variety of rose and is distinguished from the commercial comparison variety 'WEKcofbunk', also commercially known as 'All A Twitter' (U.S. Plant Pat. No. 23,324) as described in Table 2.

TABLE 2

Comparison with Commercial Line

| Characteristic | 'Zarsunorgdlt' | 'WEKcofbunk' |
|---|---|---|
| Flower color | RHS 29C (Yellow-Orange) | RHS 44C to RHS 25A |
| Plant size | 30 cm in height and 24 cm in width | 90 cm to 110 cm in height and 70 cm to 85 cm in width |

I claim:

1. A new and distinct variety of rose plant named 'Zarsunorgdlt' as illustrated and described herein.

* * * * *